United States Patent [19]

Warner et al.

[11] Patent Number: 5,716,692
[45] Date of Patent: Feb. 10, 1998

[54] LOTIONED TISSUE PAPER

[75] Inventors: Alrick Vincent Warner, Cincinnati; Thomas James Klofta, Fairfield, both of Ohio

[73] Assignee: The Procter & Gamble Co., Cincinnati, Ohio

[21] Appl. No.: 608,205

[22] Filed: Feb. 28, 1996

Related U.S. Application Data

[63] Continuation of Ser. No. 261,567, Jun. 17, 1994, abandoned.

[51] Int. Cl.$^6$ .................. B32B 3/10; B32B 29/00
[52] U.S. Cl. .................. 428/153; 428/446; 428/447; 428/452; 428/486; 428/481; 428/537.5
[58] Field of Search .................. 428/153, 537.5, 428/481, 446, 447, 452, 486

[56] References Cited

U.S. PATENT DOCUMENTS

| | | | |
|---|---|---|---|
| 3,301,746 | 1/1967 | Sanford et al. | 162/113 |
| 3,473,576 | 10/1969 | Amneus | 139/420 R |
| 3,573,164 | 3/1971 | Friedberg et al. | 162/348 |
| 3,619,280 | 11/1971 | Scheuer | 15/210.1 |
| 3,812,000 | 5/1974 | Salvucci et al. | 162/111 |
| 3,814,096 | 6/1974 | Weiss et al. | 604/289 |
| 3,818,533 | 6/1974 | Scheuer | 15/104.93 |
| 3,896,807 | 7/1975 | Buchalter | 604/289 |
| 3,916,058 | 10/1975 | Vossos | 427/389.9 |
| 3,965,518 | 6/1976 | Muoio | 15/104.93 |
| 3,974,025 | 8/1976 | Ayers | 162/113 |
| 4,085,052 | 4/1978 | Murphy et al. | 510/520 |
| 4,103,047 | 7/1978 | Zaki et al. | 427/242 |
| 4,112,167 | 9/1978 | Dake et al. | 428/154 |
| 4,142,978 | 3/1979 | Murphy | 510/519 |
| 4,191,609 | 3/1980 | Trokhan | 162/113 |
| 4,208,459 | 6/1980 | Becker et al. | 428/154 |
| 4,239,065 | 12/1980 | Trokhan | 139/383 AA |
| 4,303,471 | 12/1981 | Laursen | 162/158 |
| 4,416,950 | 11/1983 | Muller et al. | 428/532 |
| 4,462,981 | 7/1984 | Smith | 424/401 |
| 4,481,243 | 11/1984 | Allen | 428/154 |
| 4,513,051 | 4/1985 | Lavash | 428/212 |
| 4,528,239 | 7/1985 | Trokhan | 442/33 |
| 4,569,888 | 2/1986 | Muller et al. | 428/481 |
| 4,637,859 | 1/1987 | Trokhan | 162/109 |
| 4,690,821 | 9/1987 | Smith et al. | 424/401 |
| 4,732,797 | 3/1988 | Johnson et al. | 428/74 |
| 4,772,501 | 9/1988 | Johnson et al. | 428/74 |
| 4,940,513 | 7/1990 | Spendel | 162/112 |
| 4,959,125 | 9/1990 | Spendel | 162/158 |
| 5,021,405 | 6/1991 | Klimisch | 514/63 |
| 5,026,489 | 6/1991 | Snow et al. | 510/521 |
| 5,055,216 | 10/1991 | Johnson | 15/104.93 |
| 5,059,282 | 10/1991 | Ampulski et al. | 162/111 |
| 5,085,920 | 2/1992 | Nohr et al. | 428/198 |
| 5,164,046 | 11/1992 | Ampulski et al. | 162/111 |
| 5,174,927 | 12/1992 | Honsa | 510/325 |
| 5,215,626 | 6/1993 | Ampulski et al. | 162/112 |

FOREIGN PATENT DOCUMENTS

| 2019557 | 12/1990 | Canada. |
| 4-329913 AB | 11/1992 | Japan. |

*Primary Examiner*—Leszek Kiliman
*Attorney, Agent, or Firm*—Bart S. Hersko; Carl J. Roof; E. Kelly Linman

[57] ABSTRACT

A lotion composition for imparting a soft, lubricious, lotion-like feel when applied to tissue paper in amounts as low as from about 5 to about 15% by weight, and tissue paper treated with such lotion compositions are disclosed. The lotion composition comprises plastic or fluid emollient such as petrolatum, or a mixture of petrolatum with alkyl ethoxylate emollient, an immobilizing agent such as a fatty alcohol or fatty acid to immobilize the emollient on the surface of the tissue paper web and optionally a hydrophilic surfactant to improve wettability when applied to toilet tissue. Because less lotion is required to impart the desired soft, lotion-like feel benefits, detrimental effects on the tensile strength and caliper of the lotioned paper are minimized or avoided.

21 Claims, 2 Drawing Sheets

LOTIONED TISSUE PAPER

This is a continuation of application Ser. No. 08/261,567, filed on Jun. 17, 1994 now abandoned.

TECHNICAL FIELD

This application relates to lotion compositions for imparting a soft, lubricious feel to tissue paper. This application further relates to tissue paper treated with such lotion compositions.

BACKGROUND OF THE INVENTION

Cleansing the skin is a personal hygiene problem not always easily solved. Of course, the common procedure of washing the skin with soap and water works well, but at times may be either unavailable or inconvenient to use. While soap and water could be used to clean the perianal region after defecation for example, such a procedure would be extremely burdensome. Dry tissue products are therefore the most commonly used post-defecation anal cleansing product. These dry tissue products are usually referred to as "toilet tissue" or "toilet paper."

The perianal skin is marked by the presence of fine folds and wrinkles (sulci) and by hair follicles, both of which make the perianal region one of the more difficult anatomical areas to cleanse. During defecation, fecal matter is excreted through the anus and tends to accumulate in hard to reach locations such as around the base of hairs and in the sulci of the skin's surface. As the fecal matter dehydrates upon exposure to the air, or upon contact with an absorbent cleansing implement such as tissue paper, it adheres more tenaciously to the skin and hair, thus making subsequent removal of the remaining dehydrated soil even more difficult.

Failure to remove fecal matter from the anal area can have a deleterious effect on personal hygiene. The fecal matter remaining on the skin after post-defecation cleansing has a high bacterial and viral content, is malodorous and is generally dehydrated. These characteristics increase the likelihood of perianal disorders and cause personal discomfort (e.g., itching, irritation, chafing, etc.). Further, the residual fecal matter stains undergarments and causes unpleasant odors to emanate from the anal region. Thus, the consequences of inadequate perianal cleansing are clearly unattractive.

For those individuals suffering from anal disorders such as pruritis ani, hemorrhoids, fissures, cryptiris, or the like, the importance of adequate perianal cleansing takes on heightened significance. Perlanai disorders are usually characterized by openings in the skin through which the bacteria and viruses in the residual fecal matter can readily enter. Those people afflicted with anal disorders must, therefore, achieve a high degree of perianal cleansing after defecation or risk the likely result that their disorders will be aggravated by the bacteria and viruses remaining on the skin.

At the same time anal disorder sufferers face more severe consequences from insufficient post defecation cleaning, they have greater difficulty in achieving a satisfactory level of soil removal. Anal disorders generally render the perianal region extremely sensitive and attempts to remove fecal matter from this region by wiping with even normal wiping pressure causes pain and can further irritate the skin. Attempts to improve soil removal by increasing the wiping pressure can result in intense pain. Conversely, attempts to minimize discomfort by reducing the wiping pressure result in an increased amount of residual fecal matter left on the skin.

Conventional toilet tissue products used for anal cleaning are essentially dry, high density tissue papers that rely exclusively on mechanical processes to remove fecal matter from the perianal skin. These conventional products are rubbed against the perianal skin, typically with a pressure of about 1 psi (7 kilopascals) and basically scrape or abrade the fecal matter from the skin. After the first few wipes, the upper portion of the soil layer is removed because the wiping process is able to overcome the soil—soil cohesive forces that exist within the fecal matter. A cleavage is thereby created in the soil layer itself with the upper portion of the fecal layer being removed and the lower portion of the soil remaining adhered to the perianal skin.

Conventional tissue products are absorbent and with each successive wipe the fecal matter becomes increasingly dehydrated, causing it to adhere more tenaciously to the perianal skin and hair and making its removal difficult in the extreme. Pressing the tissue forcefully against the perianal skin will remove more of the fecal matter but is intensely painful for people suffering from anal disorders and can excoriate even normal perianal skin, potentially causing irritation, inflammation, pain, bleeding, and infection.

Irritation and inflammation potentially caused by the use of tissue products is not limited to toilet tissue. Facial tissue products used to wipe and remove nasal discharges associated with colds, flu and allergies can also cause such problems. In addition to difficulties in breathing, seeing, and talking, an individual afflicted with these disorders frequently has a sore and irritated nose. The nose, as well as the surrounding tissue, e.g., upper lip area, are often red and inflamed to the extent of becoming painful in extreme cases.

This irritation, inflammation and redness can have several causes. A prime one is, of course, the sheer necessity of frequently blowing one's nose into the tissue, and wiping the resultant nasal discharge from the nose and surrounding area. The degree of irritation and inflammation caused by such blowing and wiping is directly proportional to: (1) the surface roughness of the tissue used; and (2) the number of times the nose and its surrounding areas are in contact with the tissue. A tissue that is relatively weak or relatively nonabsorbent requires a greater number of contacts with the face than a stronger or more absorbent tissue that is able to contain a greater quantity of nasal discharge.

There have been numerous previous attempts to reduce the abrasive effect of toilet and facial tissues and to increase their softness impression. One common approach is by mechanical processing. By using particular processing steps during papermaking, toilet and facial tissue products can be made that are softer and less irritating. Examples of tissue products, that are mechanically processed to be softer are shown in U.S. Pat. No. 4,300,981 (Carstens), issued Nov. 17, 1981, as well as the various patents discussed in its specification.

Besides mechanical processing, others have applied emollents, salves, cleansing agents, and the like to tissue products to enhance not only the cleaning of the skin but also to reduce irritation and inflammation. This reduction in irritation and inflammation is typically achieved through either the lubricity of the substance applied to the tissue or through the therapeutic action of the substance itself. This approach is illustrated in U.S. Pat. No. 4,112,167 (Dake et al) issued Sep. 5, 1978, particularly in regard to toilet tissues. See also in U.S. Pat. No. 3,896,807 (Buchalter), issued Jul. 29, 1975 and in U.S. Pat. No. 3,814,096 (Weiss et al), issued Jun. 4, 1974 for other examples of this approach.

One substance that has been applied as a lotion to tissue products to impart a soothing, lubricious feel is mineral oil.

Mineral oil (also known as liquid petrolatum) is a mixture of various liquid hydrocarbons obtained by distilling the high-boiling (i.e., 300°–390° C.) fractions in petroleum. Mineral oil is liquid at ambient temperatures, e.g. 20°–25° C. As a result, mineral oil is relatively fluid and mobile, even when applied to tissue products Because mineral oil is fluid and mobile at ambient temperatures, it tends not to remain localized on the surface of the tissue, but instead migrates throughout. Accordingly, relatively high levels of mineral oil needs to be applied to the tissue to provide the desired softness and lotion-like feel benefits. These levels can be as high as about 22–25 wt. % of the tissue product. This leads not only to increased costs for these lotioned tissue products, but other detrimental effects as well.

One of these detrimental effects is a decrease in tensile strength of the tissue product. As mineral oil migrates to the interior of the tissue, it tends to act as a debonding agent, thus decreasing the tensile strength of the product. This debonding effect becomes more pronounced as the level of mineral oil applied is increased. Increasing the level of mineral oil applied can also adversely affect the caliper of the tissue product.

Even without increasing its level, the tendency of mineral oil to migrate once applied has other detrimental effects. For example, the applied mineral oil can transfer to, into and through the packaging or wrapper material for the lotioned toilet tissue product. This can create the need for barrier-type packaging or wrapper films to avoid smearing or other leakage of mineral oil from the tissue product.

Accordingly, it would be desirable to provide lotioned tissue products that: (1) have a desirable soothing, lubricious feel; (2) do not require relatively high levels of mineral oil: (3) do not adversely affect the tensile strength and caliper of the product; and (4) do not require special wrapping or barrier materials for packaging.

SUMMARY OF THE INVENTION

The present invention relates to a lotion composition that is semisolid or solid at ambient temperatures (i.e., at 20° C.) and imparts a soft, lubricious, lotion-like feel when applied to tissue paper. This lotion composition comprises:

(A) from about 20 to about 95% of a substantially water free emollient having a plastic or fluid consistency at 20° C. and comprising a member selected from petroleum-based emollients, fatty acid ester emollients, alkyl ethoxylate emollients, fatty acid ester ethoxylates, fatty alcohol emollients, and mixtures thereof; and (B) from about 5 to about 80% of an agent capable of immobilizing the emollient on the surface of tissue paper treated with the lotion composition, the immobilizing agent having a melting point of at least about 35° C. and comprising a member selected from the group consisting of $C_{14}$–$C_{22}$ fatty alcohols, $C_{12}$–$C_{22}$ fatty acids, $C_{12}$–$C_{22}$ fatty alcohol ethoxylates, and mixtures thereof; and (C) optionally from about 1 to about 50% of a hydrophilic surfactant having an HLB value of at least about 4.

The present invention further relates to lotioned tissue papers wherein the lotion composition is applied to at least one surface thereof in an amount of from about 2 to about 20% by weight of the dried tissue paper. Lotioned tissue papers according to the present invention have a desirable, lubricious, lotion-like feel. Because the emollient is substantially immobilized on the surface of the tissue paper, less lotion composition is needed to impart the desired soft, lotion-like feel. As a result, the detrimental effects on the tensile strength and caliper of the tissue caused by prior mineral oil-containing lotions can be avoided. In addition, special barrier or wrapping materials are unnecessary in packaging the lotioned tissue products of the present invention.

DETAILED DESCRIPTION OF THE INVENTION

Figure 1:
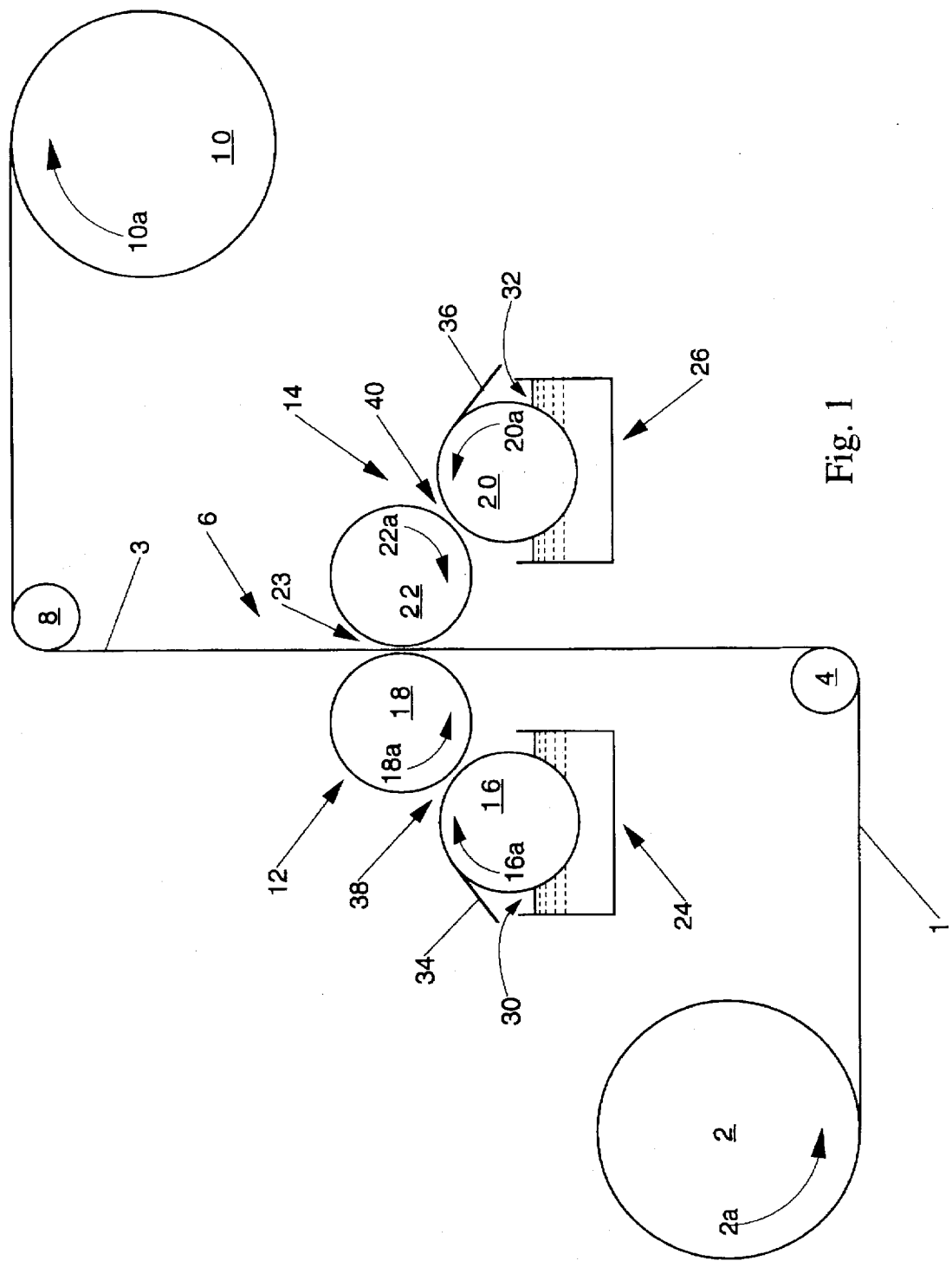
FIG. 1 is a schematic representation illustrating a preferred process for applying the lotion composition of the present invention to tissue paper webs.

As used herein, the term "comprising" means that the various components, ingredients, or steps, can be conjointly employed in practicing the present invention. Accordingly, the term "comprising" encompasses the more restrictive terms "consisting essentially of" and "consisting of."

All percentages, ratios and proportions used herein are by weight unless otherwise specified.

A. Tissue Papers

The present invention is useful with tissue paper in general, including but not limited to conventionally felt-pressed tissue paper; high bulk pattern densifted tissue paper; and high bulk, uncompacted tissue paper. The tissue paper can be of a homogenous or multi-layered construction; and tissue paper products made therefrom can be of a single-ply or multi-ply construction. The tissue paper preferably has a basis weight of between about 10 g/m$^2$ and about 65 g/m$^2$, and density of about 0.6 g/cc or less. More preferably, the basis weight will be about 40 g/m$^2$ or less and the density will be about 0.3 g/cc or less. Most preferably, the density will be between about 0.04 g/cc and about 0.2 g/cc. See Column 13, lines 61–67, of U.S. Pat. No. 5,059, 282 (Ampulski et al), issued Oct. 22, 1991, which describes how the density of tissue paper is measured. (Unless otherwise specified, all amounts and weights relative to the paper are on a dry basis.)

Conventionally pressed tissue paper and methods for making such paper are well known in the art. Such paper is typically made by depositing a papermaking furnish on a foraminous forming wire, often referred to in the art as a Fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art. In a typical process, a low consistency pulp furnish is provided from a pressurized headbox. The headbox has an opening for delivering a thin deposit of pulp furnish onto the Fourdrinier wire to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls. The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums. The tissue paper structures that are formed are referred to hereafter as conventional, pressed, tissue paper structures. Such sheets are considered to be compacted since the entire web is subjected to substantial mechanical compressional forces while the fibers are moist and are then dried while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a nonornamental configuration or can be formed so as to provide an ornamental design(s) in the tissue paper. Preferred processes for making pattern densified tissue webs are disclosed in U.S. Pat. No. 3,301,746 (Sanford et al), issued Jan. 31, 1967; U.S. Pat. No. 3,974,025 (Ayers), issued Aug. 10, 1976; and U.S. Pat. No. 4,191,609 (Trokhan) issued Mar. 4, 1980; and U.S. Pat. No. 4,637,859 (Trokhan) issued Jan. 20, 1987; all of which are incorporated by reference.

In general, pattern densified webs are preferably prepared by depositing a papermaking furnish on a foraminous forming wire such as a Fourdrinier wire to form a wet web and then juxtaposing the web against an array of supports. The web is pressed against the array of supports, thereby resulting in densified zones in the web at the locations geographically corresponding to the points of contact between the array of supports and the wet web. The remainder of the web not compressed during this operation is referred to as the high bulk field. This high bulk field can be further densified by application of fluid pressure, such as with a vacuum type device or a blow-through dryer, or by mechanically pressing the web against the array of supports. The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed. Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned displacement of knuckles that operate as the array of supports that facilitate the formation of the densified zones upon application of pressure. The pattern of knuckles constitutes the array of supports previously referred to. Suitable imprinting carrier fabrics are disclosed in U.S. Pat. No. 3,301,746 (Sanford et al), issued Jan. 31, 1967; U.S. Pat. No. 3,821,068 (Salvucci et al), issued May 21, 1974; U.S. Pat. No. 3,974,025 (Ayers), issued Aug. 10, 1976; U.S. Pat. No. 3,573,164 (Friedberg et al.), issued Mar. 30, 1971; U.S. Pat. No. 3,473,576 (Amneus), issued Oct. 21, 1969; U.S. Pat. No. 4,239,065 (Trokhan), issued Dec. 16, 1980; and U.S. Pat. No. 4,528, 239 (Trokhan), issued Jul. 9, 1985, all of which are incorporated by reference.

Preferably, the furnish is first formed into a wet web on a foraminous forming carrier, such as a Fourdrinier wire. The web is dewatered and transferred to an imprinting fabric. The furnish can alternately be initially deposited on a foraminous supporting carrier that also operates as an imprinting fabric. Once formed, the wet web is dewatered and, preferably, thermally predried to a selected fiber consistency from about 40% to about 80%. Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum. Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000 (Salvucci et al), issued May 21, 1974 and U.S. Pat. No. 4,208,459 (Becker et al), issued Jun. 17, 1980, both of which are incorporated by reference. In general, uncompacted, nonpattern-densified tissue paper structures are prepared by depositing a papermaking furnish on a foraminous forming wire such as a Fourdrinier wire to form a wet web, draining the web and removing additional water without mechanical compression until the web has a fiber consistency of at least about 80%, and creping the web. Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern-densified tissue paper structures are prepared by depositing a papermaking furnish on a foraminous wire such as a Fourdrinier wire to form a wet web, draining the web and removing additional water with the aid of a uniform mechanical compaction (pressing) until the web has a consistency of 25–50%, transferring the web to a thermal dryer such as a Yankee and creping the web. Overall, water is removed from the web by vacuum, mechanical pressing and thermal means. The resulting structure is strong and generally of singular density, but very low in bulk, absorbency and softness.

The papermaking fibers utilized for the present invention will normally include fibers derived from wood pulp. Other cellulosic fibrous pulp fibers, such as cotton linters, bagasse, etc., can be utilized and are intended to be within the scope of this invention. Synthetic fibers, such as rayon, polyethylene and polypropylene fibers, can also be utilized in combination with natural cellulosic fibers. One exemplary polyethylene fiber that can be utilized is Pulpex®, available from Hercules, Inc. (Wilmington, Del.).

Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, are preferred since they impart a superior tactile sense of softness to tissue sheets made therefrom. Pulps derived from both deciduous trees (hereafter, also referred to as "hardwood") and coniferous trees (hereafter, also referred to as "softwood") can be utilized. Also useful in the present invention are fibers derived from recycled paper, which can contain any or all of the above categories as well as other non-fibrous materials such as fillers and adhesives used to facilitate the original papermaking.

In addition to papermaking fibers, the papermaking furnish used to make tissue paper structures can have other components or materials added thereto as can be or later become known in the art. The types of additives desirable will be dependent upon the particular end use of the tissue sheet contemplated. For example, in products such as toilet paper, paper towels, facial tissues and other similar products, high wet strength is a desirable attribute. Thus, it is often desirable to add to the papermaking furnish chemical substances known in the art as "wet strength" resins.

A general dissertation on the types of wet strength resins utilized in the paper art can be found in TAPPI monograph series No. 29, Wet Strength in Paper and Paperboard, Technical Association of the Pulp and Paper Industry (New York, 1965). The most useful wet strength resins have generally been cationic in character. For permanent wet strength generation, polyamide-epichlorohydrin resins are cationic wet strength resins have been found to be of particular utility. Suitable types of such resins are described in U.S. Pat. No. 3,700,623 (Keim), issued Oct. 24, 1972, and U.S. Pat. No. 3,772,076 (Keim), issued Nov. 13, 1973, both of which are incorporated by reference. One commercial source of a useful polyamide-epichlorohydrin resin is Hercules, Inc. of Wilmington, Del., which markets such resins under the mark Kymene®557H.

Polyacrylamide resins have also been found to be of utility as wet strength resins. These resins are described in U.S. Pat. Nos. 3,556,932 (Coscia et al), issued Jan. 19, 1971, and 3,556,933 (Williams et al), issued Jan. 19, 1971, both of which are incorporated herein by reference. One commercial source of polyacrylamide resins is American Cyanamid Co. of Stamford, Conn., which markets one such resin under the mark Parez®631 NC.

Still other water-soluble cationic resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins can also find utility in the present invention. In addition, temporary wet strength resins such as Caldas 10 (manufactured by Japan Carlit) and CoBond 1000 (manufactured by National Starch and Chemical Company) can be used in the present invention. It is to be understood that the addition of chemical compounds such as the wet strength and temporary wet strength resins discussed above to the pulp furnish is optional and is not necessary for the practice of the present invention.

In addition to wet strength additives, it can also be desirable to include in the papermaking fibers certain dry strength and lint control additives known in the art. In this regard, starch binders have been found to be particularly suitable. In addition to reducing linting of the finished tissue paper product, low levels of starch binders also impart a modest improvement in the dry tensile strength without imparting stiffness that could result from the addition of high levels of starch. Typically the starch binder is included in an amount such that it is retained at a level of from about 0.01 to about 2%, preferably from about 0.1 to about 1%, by weight of the tissue paper.

In general, suitable starch, binders for the present invention are characterized by water solubility and hydrophilicity. Although it is not intended to limit the scope of suitable starch binders, representative starch materials include corn starch and potato starch, with waxy corn starch known industrially as amioca starch being particularly preferred. Amioca starch differs from common corn starch in that it is entirely amylopectin, whereas common corn starch contains both amylopectin and amylose. Various unique characteristics of amioca starch are further described in "Amioca—The Starch From Waxy Corn", H. H. Schopmeyer, Food Industries, December 1945, pp. 106–108 (Vol. pp. 1476–1478).

The starch binder can be in granular or dispersed form, the granular form being especially preferred. The starch binder is preferably sufficiently cooked to induce swelling of the granules. More preferably, the starch granules are swollen, as by cooking, to a point just prior to dispersion of the starch granule. Such highly swollen starch granules shall be referred to as being "fully cooked." The conditions for dispersion in general can vary depending upon the size of the starch granules, the degree of crystallinity of the granules, and the amount of amylose present. Fully cooked amioca starch, for example, can be prepared by heating an aqueous slurry of about 4% consistency of starch granules at about 190° F. (about 88° C.) for between about 30 and about 40 minutes. Other exemplary starch binders that can be used include modified cationic starches such as those modified to have nitrogen containing groups, including amino groups and methylol groups attached to nitrogen, available from National Starch and Chemical Company, (Bridgewater, N.J.), that have previously been used as pulp furnish additives to increase wet and/or dry strength.

B. Lotion Composition

The lotion compositions of the present invention are solid, or more often semisolid, at 20° C., i.e. at ambient temperatures. By "semisolid" is meant that the lotion composition has a rheology typical of pseudoplastic or plastic fluids. When no shear is applied, the lotion compositions can have the appearance of a semi-solid but can be made to flow as the shear rate is increased. This is due to the fact that, while the lotion composition contains primarily solid components, it also includes some minor liquid components.

By being solid or semisolid at ambient temperatures, these lotion compositions do not have a tendency to flow and migrate into the interior of the tissue web to which they are applied. This means less lotion composition is required for imparting softness and lotion-like feel benefits. It also means there less chance for debonding of the tissue paper that can potentially lead to decreases in tensile strength.

When applied to tissue paper, the lotion compositions of the present invention impart a soft, lubricious, lotion like feel to the user of the paper. This particular feel has also been characterized as "silky", "slick", "smooth", etc. Such a lubricious, lotion-like feel is particularly beneficial for those having more sensitive skin due to chronic conditions such as skin dryness or hemorrhoids, or due to more transient conditions such as colds or allergies.

The lotion compositions of the present invention comprise: (1) an emollient(s); (2) an immobilizing agent(s) for the emollient; (3) optionally a hydrophilic surfactant(s); and (4) other optional components:

1. Emollient

The key active ingredient in these lotion compositions is one or more emollients. As used herein, an emollient is a material that softens, soothes, supples, coats, lubricates, moisturizes, or cleanses the skin. An emollient typically accomplishes several of these objectives such as soothing, moisturizing, and lubricating the skin. For the purposes of the present invention, these emollients have either a plastic or fluid consistency at 20° C., i.e., at ambient temperatures. This particular emollient consistency allows the lotion composition to impart a soft, lubricious, lotion-like feel.

The emollients useful in the present invention are also substantially free of water. By "substantially free of water" is meant that water is not intentionally added to the emollient. Addition of water to the emollient is not necessary in preparing or using the lotion compositions of the present invention and could require an additional drying step. However, minor or trace quantities of water in the emollient that are picked up as a result of, for example, ambient humidity can be tolerated without adverse effect. Typically, the emollients used in the present invention contain about 5% or less water, preferably about 1% or less water, most preferably about 0.5% or less water.

Emollients useful in the present invention can be petroleum-based, fatty acid ester type, alkyl ethoxylate type, fatty acid ester ethoxylates, fatty alcohol type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum is a particularly preferred emollient for lotion compositions of the present invention.

Suitable fatty acid ester type emollients include those derived from $C_{12}-C_{28}$ fatty acids, preferably $C_{16}-C_{22}$ saturated fatty acids, and short chain ($C_1-C_8$, preferably $C_1-C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}-C_{28}$, preferably $C_{12}-C_{16}$) and shorter chain fatty acids e.g., lactic acid, such as lauryl lactate and cetyl lactate.

Suitable alkyl ethoxylate type emollients include $C_{12}-C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (acetyl alcohol ethoxylate having an average degree of ethoxylation of 10) and steareth-10 (a stearyl alcohol ethoxylate having an average degree of ethoxylation of 10). These alkyl ethoxylate emollients are typically used in combination with the petroleum-based emollients, such as petrolatum, at a weight ratio of alkyl ethoxylate emollient to petroleum-based emotlient of from about 1:1 to about 1:5, preferably from about 1:2 to about 1:4.

Suitable fatty alcohol type emollients include $C_{12}-C_{22}$ fatty alcohols, preferably $C_{16}-C_{18}$ fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Besides petroleum-based emollients, fatty acid ester emollients, fatty acid ester ethoxylates, alkyl ethoxylate emollients and fatty alcohol emollients, the emollients useful in the present invention can include minor amounts (e.g., up to about 10% of the total emollient) of other, conventional emollients. These other, conventional emollients include propylene glycol, glycerine, triethylene glycol, spermaceti or other waxes, fatty acids, and fatty alcohol ethers having from 12 to 28 carbon atoms in their fatty chain, such as stearic acid, propoxylated fatty alcohols; glycerides, acetoglycerides, and ethoxylated glycerides of $C_{12}-C_{28}$ fatty acids; other fatty esters of polyhydroxy alcohols; lanolin and its derivatives; silicone polyether copolymers, and polysiloxanes having a viscosity at 20° C. of from about 5 to about 2,000 centistokes such as disclosed in U.S. Pat. No. 5,059, 282 (Ampulski et al), issued Oct. 22, 1991, which is incorporated by reference. These other emollients should be included in a manner such that the solid or semisolid characteristics of the lotion composition are maintained.

The amount of emollient that can be included in the lotion composition will depend on a variety of factors, including the particular emollient involved, the lotion-like benefits desired, the other components in the lotion composition and like factors. The lotion composition can comprise from about 20 to about 95% of the emollient. Preferably, the lotion composition comprises from about 30 to about 80%, most preferably from about 40 to about 75%, of the emollient.

2. Immobilizing Agent

An especially key component of the lotion compositions of the present invention is an agent capable of immobilizing the emollient on the surface of the paper to which the lotion composition is applied. Because the emollient in the composition has a plastic or fluid consistency at 20° C., it tends to flow or migrate, even when subjected to modest shear. When applied to a tissue paper web, especially in a melted or molten state, the emollient will not remain primarily on the surface of the paper. Instead, the emollient will tend to migrate and flow into the interior of the paper web.

This migration of the emollient into the interior of the web can cause undesired debonding of the paper by interfering with the normal hydrogen bonding that takes place between the paper fibers. This usually leads to a decrease in tensile strength of the paper. It also means much more emollient has to be applied to the paper web to get the desired lubricious, lotion-like feel benefits. Increasing the level of emollient not only increases the cost, but also exacerbates the debonding problem of the paper.

The immobilizing agent counteracts this tendency of the emollient to migrate or flow by keeping the emollient primarily localized on the surface of the tissue paper web to which the lotion composition is applied. This is believed to be due, in part, to the fact that the immobilizing agent forms hydrogen bonds with the tissue paper web. Through this hydrogen bonding, the immobilizing agent becomes localized on the surface of the paper. Since the immobilizing agent is also miscible with the emollient (or solubilized in the emollient with the aid of an appropriate emulsifier), it entraps the emollient on the surface of the paper as well.

It is also advantageous to "lock" the immobilizing agent on the surface of the paper. This can be accomplished by using immobilizing agents which quickly crystallize (i.e., solidify) at the surface of the paper. In addition, outside cooling of the treated paper via blowers, fans, etc. can speed up crystallization of the immobilizing agent.

In addition to being miscible with (or solubilized in) the emollient, the immobilizing agent needs to have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

The viscosity of the immobilizing agent should also be as high as possible to keep the lotion from flowing into the interior of the paper. Unfortunately, high viscosities can also lead to lotion compositions that are difficult to apply without processing problems. Therefore, a balance must be achieved so the viscosities are high enough to keep the immobilizing agent localized on the surface of the paper, but not so high as to cause processing problems. Suitable viscosities for the iramobilizing agent will typically range from about 5 to about 200 centipoises, preferably from about 15 to about 100 centipoises, measured at 60° C.

Suitable immobilizing agents for the present invention can comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include $C_{16}$–$C_{18}$ fatty acids, most preferably selected from the group consisting of cetyl acid, stearyl acid, and mixtures thereof. Mixtures of cetyl acid and stearyl acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear.

Importantly, these preferred immobilizing agents such as the $C_{16}$–$C_{18}$ fatty alcohols increase the rate of crystallization of the lotion causing the lotion to crystallize rapidly onto the surface of the substrate. Lower lotion levels can therefore be utilized or a superior lotion feel can be delivered. Traditionally, greater amounts of lotion were needed to generate softness because of the flow of these liquids into the bulk paper substrate.

Optionally, other types of immobilizing agents can be used in combination with the fatty alcohols, fatty adds, and fatty alcohol ethoxylates described above. Typically, only minor amounts of these other types of immobilizing agents would be used (i.e., up to about 10% of the total immobilizing agent). Examples of these other types of immobilizing agents includes polyhydroxy fatty acid esters, polyhydroxy fatty acid amides, and mixtures thereof. To be useful as immobilizing agents, the polyhydroxy moiety of the ester or amide should have at least one free hydroxy group. It is believed that these free hydroxy group(s) are the ones that co-crosslink through hydrogen bonds with the cellulosic fibers of the tissue paper web to which the lotion composition is applied and homo-crosslink, also through hydrogen bonds, the hydroxy groups of the alcohol, acid, ester or amide, thus entrapping and immobilizing the other components in the lotion matrix.

It is also believed that molecules such as long chain fatty alcohols can orient themselves and interact with one another to form a lamellar structure. In this lamellar structure, the hydroxyl groups and alkyl chains of neighboring alcohol molecules orient and interact with one another to form an organized structure. In this "packing arrangement," the hydroxyl groups of the alcohols form hydrogen bonds with the cellulose polar functionalities (e.g., hydroxy or carbonyl) to "immobilize" the alcohols at the paper's surface. Since the alcohols are miscible with the preferred emollients, anchoring and/or immobilization of the emollient will occur.

Preferred esters and amides will have three or more free hydroxy groups on the polyhydroxy moiety and are typically nonionic in character. Because of the possible skin sensitivity of those using paper products to which the lotion composition is applied, these esters and amides should also be relatively mild and non-irritating to the skin.

Suitable polyhydroxy fatty acid esters for use in the present invention will have the formula:

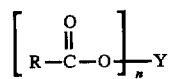

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters are particularly preferred and include sucrose monostearate and sucrose monolaurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably C1 alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably, will be selected from the group consisting of —$CH_2$—(CHOH)$_n$—$CH_2OH$, —CH($CH_2OH$) —[(CHOH)$_{n-1}$]—$CH_2OH$, —$CH_2OH$—$CH_2$—(CHOH)$_2$ ($CHOR^3$)(CHOH)—$CH_2OH$, where n is an integer from 3 to 5, and $R^3$ is H or a cyclic or aliphatic monosaccharide. Most preferred are the glycityls where n is 4, particularly —$CH_2$—(CHOH)$_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl, $R^2$ can be selected to provide, for example, cocamides, stearamides, oleamides, lauramides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

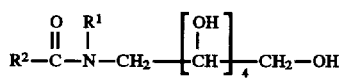

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2. (polyethylene glycol ethers of stearyl alcohol that conform to the formula $CH_3(CH_2)_{17}$ $(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of steareth-2 and sorbitan tristearate as the emulsifier.

The amount of immobilizing agent that should be included in the lotion composition will depend on a variety of factors, including the particular emollient involved, the particular immobilizing agent involved, whether an emulsifier is required to solubilize the immobilizing agent in the emollient, the other components in the lotion composition and like factors. The lotion composition can comprise from about 5 to about 80% of the immobilizing agent. Preferably, the lotion composition comprises from about 5 to about 50%, most preferably from about 10 to about 40%, of the immobilizing agent.

3. Optional Hydrophilic Surfactant

In many instances, lotion compositions according to the present invention will be applied to tissue paper webs that will be used as toilet tissue. In such cases, it is highly desirable that the paper web treated with the lotion composition be sufficiently wettable. Depending upon the particular immobilizing agent used in the lotion composition of the present invention, an additional hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 will require addition of hydrophilic surfactant to improve wettability if the lotion composition is applied to paper webs used as toilet tissue. Similarly, a hydrophobic emollient such as petrolatum will require the addition of a hydrophilic surfactant.

Suitable hydrophilic surfactants will be miscible with the emollient and the immobilizing agent so as to form homogeneous mixtures. Because of possible skin sensitivity of those using paper products to which the lotion composition is applied, these surfactants should also be relatively mild and non-irritating to the skin. Typically, these hydrophilic surfactants are nonionic to be not only non-irritating to the skin, but also to avoid other undesirable effects on the tissue paper, e.g., reductions in tensile strength.

Suitable nonionic surfactants will be substantially non-migratory after the lotion composition is applied to the tissue paper web and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of tissue paper products, e.g., at least about 30° C. In this regard, these nonionic surfactants will preferably have melting points similar to those of the immobilizing agents previously described.

Suitable nonionic surfactants for use in lotion compositions of the present invention include alkylglycosides; alkylglycoside ethers as described in U.S. Pat. No. 4,011,389 (Langdon, et al), issued Mar. 8, 1977; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 76 (i.e., Steareth-10) and Brij 56 (i.e., Cetyl-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes Aerosol OT, a dioctyl ester of sodium sulfosuccinic acid marketed by American Cyanamid Company.

Still another type of suitable surfactant for use in the present invention includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition.

The amount of hydrophilic surfactant required to increase the wettability of the lotion composition to a desired level will depend upon the HLB value and level of immobilizing agent used, the HLB value of the surfactant used and like factors. The lotion composition can comprise from about 1 to about 50% of the hydrophilic surfactant when needed to increase the wettability properties of the composition. Preferably, the lotion composition comprises from about 1 to about 25%, most preferably from about 10 to about 20%, of the hydrophilic surfactant when needed to increase wettability.

4. Other Optional Components

Lotion compositions can comprise other optional components typically present in emollient, creams, and lotions of this type. These optional components include water, viscosity modifiers, perfumes, disinfectant antibacterial actives, pharmaceutical actives, film formers, deodorants, opacifiers, astringents, solvents and the like. In addition, stabilizers can be added to enhance the shelf life of the lotion composition such as cellulose derivatives, proteins and lecithin. All of these materials are well known in the art as additives for such formulations and can be employed in appropriate amounts in the lotion compositions of the present invention.

C. Treating Tissue Paper with Lotion Composition

In preparing lotioned paper products according to the present invention, the lotion composition is applied to at least one surface of a tissue paper web. Any of a variety of application methods that evenly distribute lubricious materials having a molten or liquid consistency can be used. Suitable methods include spraying, printing (e.g., flexographic printing), coating (e.g., gravure coating), extrusion, or combinations of these application techniques, e.g. spraying the lotion composition on a rotating surface, such as a calender roll, that then transfers the composition to the surface of the paper web. The lotion composition can be applied either to one surface of the tissue paper web, or both surfaces. Preferably, the lotion composition is applied to both surfaces of the paper web.

The manner of applying the lotion composition to the tissue paper web should be such that the web does not become saturated with the lotion composition. If the web becomes saturated with the lotion composition, there is a greater potential for debonding of the paper to occur, thus leading to a decrease in the tensile strength of the paper. Also, saturation of the paper web is not required to obtain the softness and lotion-like feel benefits from the lotion composition of the present invention. Particularly suitable application methods will apply the lotion composition primarily to the surface, or surfaces of the paper web.

The lotion composition can be applied to the tissue paper web after the web has been dried, i.e. a "dry web" addition method. The lotion composition is applied in an amount of from about 2 to about 30% by weight of the tissue paper web. Preferably, the lotion composition is applied in an amount of from about 5 to about 20% by weight of the tissue paper web, most preferably from about 10 to about 16% by weight of the web. Such relatively low levels of lotion composition are adequate to impart the desired softness and lotion-like feel benefits to the tissue paper, yet do not saturate the tissue paper web to such an extent that absorbency, wettability and particularly, strength, are substantially affected.

The lotion composition can also be applied nonuniformly to the surface(s) of the tissue paper web. By "nonuniform" is meant that the amount, pattern of distribution, etc. of the lotion composition can vary over the surface of the paper. For example, some podions of the surface of the tissue paper web can have greater or lesser amounts of lotion composition, including portions of the surface that do not have any lotion composition on it.

The lotion composition can be applied to the tissue paper web at any point after it has been dried. For example, the lotion composition can be applied to the tissue paper web after it has been creped from a Yankee dryer, but prior to calendering, i.e., before being passed through calender rolls. The lotion composition can also be applied to the paper web after it has passed through such calender rolls and prior to being wound up on a parent roll. Usually, it is preferred to apply the lotion composition to the tissue paper as it is being unwound from a parent roll and prior to being wound up on smaller, finished paper product rolls.

The lotion composition is typically applied from a melt thereof to the tissue paper web. Since the lotion composition melts at significantly above ambient temperatures, it is usually applied as a heated coating to the tissue paper web. Typically, the lotion composition is heated to a temperature in the range from about 35° to about 100° C., preferably from 40° to about 90° C., prior to being applied to the tissue paper web. Once the melted lotion composition has been applied to the tissue paper web, it is allowed to cool and solidify to form solidified coating or film on the surface of the paper.

In applying lotion compositions of the present invention to tissue paper webs, gravure coating and extrusion coating methods are preferred. FIG. 1 illustrates one such preferred method involving gravure coating. Referring to FIG. 1, a dried tissue web 1 is unwound from parent tissue roll 2 (rotating in the direction indicated by arrow 2a) and advanced around turning roll 4. From turning roll 4, web 1 is advanced to offset-gravure coating station 6 where the lotion composition is then applied to both sides of the web. After leaving station 6, web 1 becomes a lotioned web indicated by 3. Lotioned web 3 is then advanced around turning roll 8 and then wound up on lotioned tissue parent roll 10 (rotating in the direction indicated by arrow 10a).

Station 6 comprises a pair of linked offset-gravure presses 12 and 14. Press 12 consists of a lower gravure cylinder 16 and an upper offset cylinder 18; press 14 similarly consists of a lower gravure cylinder 20 and an upper offset cylinder 22. Gravure cylinders 16 and 20 each have a specific etched cell pattern and size, and each have a chrome plated surface, while offset cylinders 18 and 22 each have a smooth polyurethane rubber surface. The size of the cell volume of the gravure roll will depend upon the desired coat weight, line speed, and lotion viscosity. Both the gravure and offset cylinders are heated to keep the lotion molten. These gravure and offset cylinders rotate in the directions indicated by arrows 16a, 18a, 20a and 22a, respectively. As shown in FIG. 1, offset cylinders 18 and 22 are directly opposite and parallel to each other and provide a nip area indicated by 23 through which web 1 passes.

Positioned beneath gravure cylinders 16 and 20 are fountain trays 24 and 26, respectively. Hot, molten (e.g., 65° C.) lotion composition is pumped into each of these heated trays 24 and 26 to provide reservoirs of the molten lotion composition, as indicated arrows by 30 and 32, respectively. As gravure cylinders 16 and 20 rotate in the directions indicated by arrows 16a and 20a within reservoirs 30 and 32, they pick up a quantity of molten lotion composition. Excess lotion on each of the gravure cylinders 16 and 20 is then removed by doctor blades 34 and 36, respectively.

The lotion composition remaining in the heated gravure cylinder cells 16 and 20 is then transferred to heated offset cylinders 18 and 22 (rotating in the opposite direction as indicated by arrows 18a and 22b) in nip areas 38 and 40 between the respective pairs of cylinders. The lotion composition transferred to offset cylinders 18 and 22 is then simultaneously transferred to both sides of web 1. The amount of lotion composition transferred to web 1 can be controlled by: (1) adjusting the width of nip area 23 between offset cylinders 18 and 22; and/or (2) adjusting the width of nip areas 38 and 40 between gravure/offset cylinder pairs 16/18 and 20/22.

Figure 2:
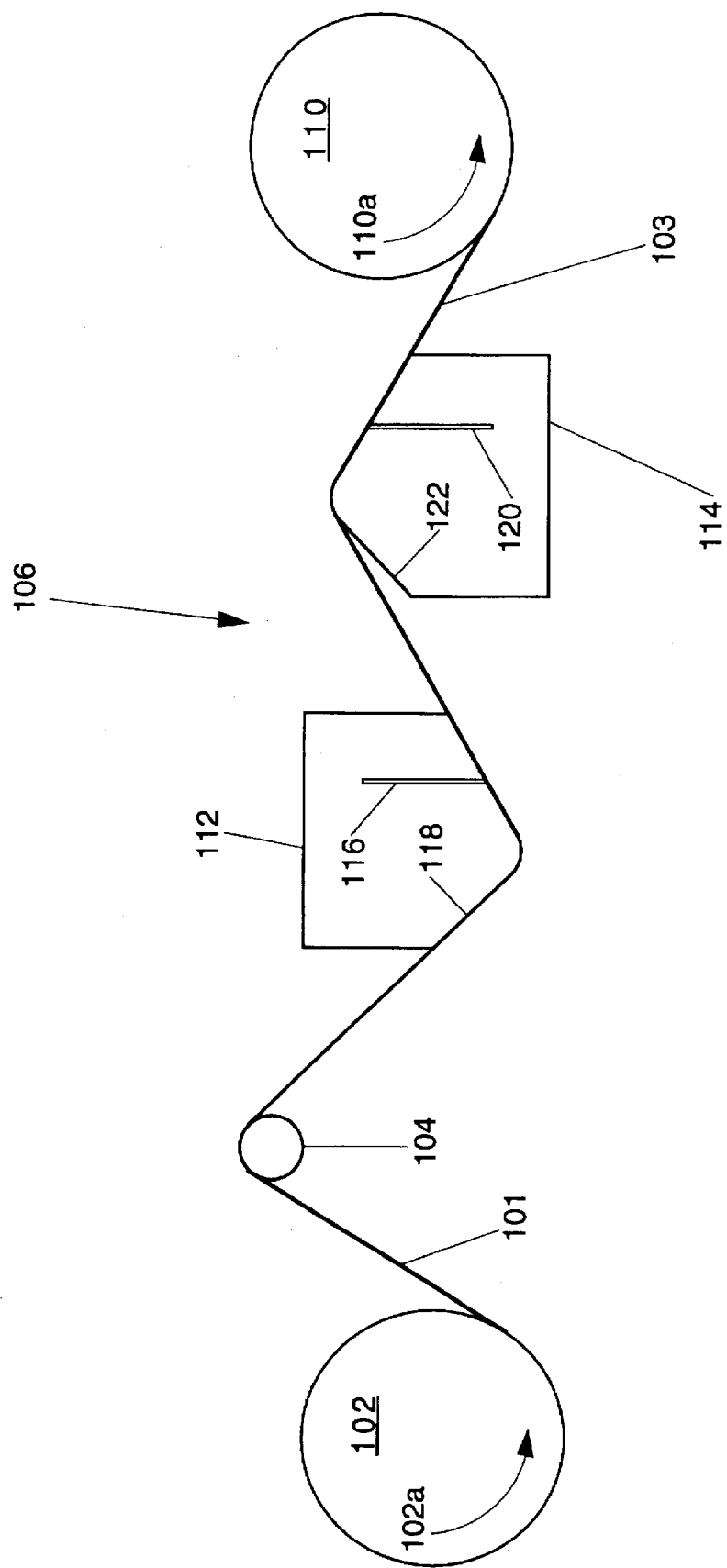
FIG. 2 is a schematic representation illustrating an alternative process for applying the lotion composition of the present invention to tissue paper webs.

FIG. 2 illustrates an alternative preferred method involving slot extrusion coating. Referring to FIG. 2, a dried tissue web 101 is unwound from parent tissue roll 102 (rotating in the direction indicated by arrow 102a) and then advanced around turning roll 104. From turning roll 104, web 101 is advanced to slot extrusion coating station 106 where the lotion composition is then applied to both sides of the web. After leaving station 106, web 101 becomes a lotioned web indicated by 103. Lotioned web 103 is then wound up on lotioned tissue parent roll 110 (rotating in the direction indicated by arrow 110a).

Station 106 comprises a pair of spaced slot extruders 112 and 114. Extruder 112 has an elongated slot 116 and a web contacting surface 118; extruder 114 similarly has an elongated slot 120 and a web contacting surface 122. As shown in FIG. 2, extruders 112 and 114 are oriented such that surface 118 is in contact with one side of web 101, while surface 122 is in contact with the other side of web 101. Hot, molten (e.g., 65° C.) lotion composition is pumped to each of extruders 112 and 114 and is then extruded through slots 116 and 120, respectively.

As web 101 passes over the heated surface 118 of extruder 112 and reaches slot 116, the molten lotion composition extruded from slot 116 is applied to the side of web 101 in contact with surface 118. Similarly, as web 101 passes over heated surface 122 of extruder 114 and reaches slot 120, the molten lotion composition extruded from slot 120 is applied to the side of web 101 in contact with surface 122. The amount of lotion composition transferred to web 101 is controlled by: (1) the rate at which the molten lotion composition is extruded from slots 116 and 122; and/or (2) the speed at which web 101 travels while in contact with surfaces 118 and 122.

SPECIFIC ILLUSTRATIONS OF THE PREPARATION OF LOTIONED TISSUE PAPER ACCORDING TO THE PRESENT INVENTION

The following are specific illustrations of treating tissue paper with lotion compositions in accordance with the present invention:

EXAMPLE 1

A. Preparation of Lotion Compositions

Two water free lotion compositions (Lotion A and Lotion B) are made by mixing the following melted (i.e., liquid) components together: White Protoper® 1S (white petrolatum made by Witco Corp.), Cetearyl Alcohol (a mixed linear $C_{16}$–$C_{18}$ primary alcohol made by the Procter & Gamble Company under the name TA-1618); Steareth-10 (Brij 76, a $C_{18}$ linear alcohol ethoxylate having an average degree of ethoxylation of 10, made by ICI America); and Aloe (in mineral oil by Dr. Madis Laboratories). The weight percentages of these components are shown in Table I below:

TABLE I

| Component | Lotion A Weight % | Lotion B Weight % |
|---|---|---|
| White Protopet ® 1S | 49 | 39 |
| Cetearyl Alcohol | 35 | 40 |
| Steareth-10 | 15 | 20 |
| Aloe | 1 | 1 |

B. Preparation of Lotioned Tissue by Hot Melt Spraying

Lotions A or B are placed into a PAM 600S Spraymatic hot melt spray gun (made by PAM Fastening Technology, Inc.) operating at a temperature of 90° C. Twelve inch by 12 inch sheets of tissue paper substrate are spray coated to the desired lotion level on each side of the substrate. The lotioned tissues are then placed in a 70° C. convection oven for 30 seconds after each side are sprayed to remove volatile components, and to insure a more even coating of the lotion onto the paper fibers.

EXAMPLE 2

A. Preparation of Lotion Composition

A water free lotion composition (Lotion C) is made by mixing together the melted (i.e., liquid) components in the weight percentages shown in Table II below. The components are combined at room temperature in a 1 quart plastic container. The container is sealed and placed in an oven at 70° C. until all components are melted. This melted mass is mixed/shaken thoroughly to produce a homogenous mixture. The resulting lotion composition is maintained in a 60° C. oven until ready for use.

TABLE II

| Component | Weight % |
|---|---|
| White Protopet ® 1S | 48 |
| Cetearyl Alcohol | 35 |
| Steareth-10 | 15 |
| GE SF1188* | 1 |
| Aloe | 1 |

*A silicone polyether copolymer made by GE

B. Preparation of Lotioned Tissue by Hot Melt Spraying

Melted Lotion C is placed into a PAM 600S Spraymatic hot melt spray gun operating at a temperature of 90° C. A 12 inch by 12 inch sheet of tissue paper substrate is spray coated to the desired lotion level on each side of the substrate. The lotioned tissue is placed in a 70° C. convection oven for 30 seconds after each side is sprayed to remove volatile components, and to insure a more even coating of the lotion onto the paper fibers.

EXAMPLE 3

A. Preparation of Lotion Composition

A water free lotion composition (Lotion D) is made by mixing together the melted (i.e., liquid) components in the weight percentages shown in the Table III below according to the procedure of Example 2:

TABLE III

| Component | Weight % |
|---|---|
| White Protopet ® 1S | 48 |
| Cetearyl Alcohol | 35 |
| Steareth-10 | 15 |
| Aerosol OT-100* | 1 |
| Aloe | 1 |

*A dioctyl ester of sodium sulfosuccinic acid made by American Cyanamid

B. Preparation of Lotioned Tissue by Hot Melt Spraying

Melted Lotion D is spray coated to the desired lotion level on each side of a paper tissue substrate according to the procedure of Example 2. The lotioned tissue is then placed in a 70° C. convection oven for 30 seconds after each side is sprayed to remove volatile components, and to insure a more even coating of the lotion onto the paper fibers.

EXAMPLE 4

A. Preparation of Lotion Composition

A water free lotion composition (Lotion E) is made from the following components in the amounts shown in Table IV below according to the procedure of Example 2:

TABLE IV

| Component | Weight % |
|---|---|
| Petrolatum* | 57 |
| Stearic Acid | 23 |
| Steareth-10 | 18 |
| GE SF1228 | 1 |
| Aloe | 1 |

*White Protopet ® 1S from Witco

B. Preparation of Lotioned Tissue by Hot Melt Spraying

Melted Lotion E is spray coated to the desired lotion level on each side of a paper tissue substrate according to the procedure of Example 2. The lotioned tissue is then placed in a 55° C. convection oven for 15 seconds after each side is sprayed to remove volatile components, and to insure a more even distribution of the lotion components onto the paper fibers.

What is claimed is:

1. A lotioned tissue paper having applied to at least one surface thereof, in an amount of from about 2 to about 20% by weight of the dried tissue paper, a lotion composition for treating tissue paper which is semi-solid or solid at 20° C. and which comprises:

(A) from about 20 to about 95% of a substantially water free petrolatum emollient having a plastic or fluid consistency at 20° C.;

(B) from about 5 to about 80% of an agent capable of immobilizing said petrolatum emollient on the surface of the tissue paper, said immobilizing agent having a melting point of at least about 35° C. and comprising a member selected from the group consisting of $C_{14}$–$C_{22}$ fatty alcohols, $C_{12}$–$C_{22}$ fatty acids, and mixtures thereof;

(C) from about 1 to about 50% of a nonionic hydrophilic surfactant having an HLB value of at least about 4, wherein said hydrophilic surfactant is selected from the group consisting of ethoxylated alcohols having an alkyl chain of from about 8 to about 22 carbon atoms and having an average degree of ethoxylation ranging from about 1 to about 54, and ethoxylated sorbitan esters of $C_{12}$–$C_{18}$ fatty acids having an average degree of ethoxylation of from about 2 to about 20; and (D) from about 1 to about 50% of an additional hydrophilic surfactant selected from the group consisting of a dioctyl ester of sodium sulfosuccinic acid, silicone polyether copolymer, and mixtures thereof.

2. The lotioned paper of claim 1 which has from about 5 to about 20% by weight of said lotion composition applied to said at least one surface of the tissue paper.

3. The lotioned paper of claim 1 wherein said lotion composition comprises from about 30 to about 85% of said petrolatum emollient.

4. The lotioned paper of claim 3 wherein said petrolatum emollient contains about 5% or less water.

5. The lotioned paper of claim 1 wherein said lotion composition comprises from about 5 to about 50% of said immobilizing agent, said immobilizing agent having a melting point of at least about 40° C.

6. The lotioned paper of claim 5 wherein said immobilizing agent comprises a $C_{14}$–$C_{22}$ fatty alcohol.

7. The lotioned paper of claim 6 wherein said immobilizing agent comprises a $C_{16}$–$C_{18}$ fatty alcohol.

8. The lotioned paper of claim 7 wherein said immobilizing agent comprises a $C_{16}$–$C_{18}$ fatty alcohol selected from the group consisting of cetyl alcohol, stearyl alcohol, and mixtures thereof.

9. The lotioned paper of claim 8 wherein said immobilizing agent comprises a mixture of cetyl alcohol and stearyl alcohol.

10. The lotioned paper of claim 1 wherein said hydrophilic surfactant comprises an ethoxylated alcohol having an alkyl chain of from about 8 to about 22 carbon atoms and having an average degree of ethoxylation ranging from about 1 to about 54.

11. The lotioned paper of claim 10 wherein said ethoxylated alcohol has a alkyl chain of from about 11 to about 22 carbon atoms and having an average degree of ethoxylation ranging from about 2 to about 30.

12. The lotioned paper of claim 1 wherein said hydrophilic surfactant comprises an ethoxylated sorbitan ester of a $C_{12}$–$C_{18}$ fatty acid having an average degree of ethoxylation of from about 2 to about 20.

13. The lotioned paper of claim 12 wherein said ethoxylated sorbitan ester has an average degree of ethoxylation of from about 2 to about 10.

14. The lotioned paper of claim 5 wherein said immobilizing agent comprises a $C_{12}$–$C_{22}$ fatty acid.

15. The lotioned paper of claim 14 wherein said immobilizing agent is a $C_{16}$–$C_{18}$ fatty acid.

16. The lotioned paper of claim 15 wherein said immobilizing agent is $C_{16}$–$C_{18}$ fatty acid selected from cetyl acid, stearic acid, and mixtures thereof.

17. The lotioned paper of claim 1 wherein said additional hydrophilic surfactant is a dioctyl ester of sodium sulfosuccinic acid.

18. The lotioned paper of claim 1 wherein said additional hydrophilic surfactant is a silicone polyether copolymer.

19. The lotioned paper of claim 8 wherein said additional hydrophilic surfactant is a dioctyl ester of sodium sulfosuccinic acid.

20. The lotioned paper of claim 8 wherein said additional hydrophilic surfactant is a silicone polyether copolymer.

21. The lotioned paper of claim 10 wherein said additional hydrophilic surfactant is a dioctyl ester of sodium sulfosuccinic acid and wherein said immobilizing agent comprises a mixture of cetyl alcohol and stearyl alcohol.

* * * * *

UNITED STATES PATENT AND TRADEMARK OFFICE
CERTIFICATE OF CORRECTION

PATENT NO. : 5,716,692

DATED : Feb. 10, 1998

INVENTOR(S) : A. V. Warner et al.

It is certified that error appears in the above-identified patent and that said Letters Patent is hereby corrected as shown below:

On the Title page, line 8 of the ABSTRACT, "emoilient" should read --emollient--.

Column 1, line 47 "cryptiris" should read --cryptitis--.

Column 1, line 49 "Perlanai" should read --Perianal--.

Column 2, line 55 "emollents" should read --emollients--.

Column 4, line 31 "densifted" should read --densified--.

Column 5, line 9 "densifted" should read --densified--.

Column 5, line 11 "densifted" should read --densified--.

Column 5, line 13 "densifted" should read --densified--.

Column 5, line 14 "densifted" should read --densified--.

Column 5, line 19 "densifted" should read --densified--.

Column 5, line 25 "densifted" should read --densified--.

Column 5, line 30 "densifted" should read --densified--.

Column 5, line 45 "densifted" should read --densified--.

Column 5, line 47 "densifted" should read --densified--.

UNITED STATES PATENT AND TRADEMARK OFFICE
CERTIFICATE OF CORRECTION

PATENT NO. : 5,716,692
DATED : Feb. 10, 1998
INVENTOR(S) : A.V. Warner, et al

It is certified that error appears in the above-identified patent and that said Letters Patent is hereby corrected as shown below:

Column 5, line 51 "densifted" should read --densified--.

Column 5, line 56 "densifted" should read --densified--.

Column 8, line 1 "starch," should read --starch--.

Column 9, line 57 "acetyl" should read --a cetyl--.

Column 9, line 63 "emotlient" should read --emollient--.

Column 11, line 23 "iramobilizing" should read --immobilizing--.

Column 11, line 54 "adds" should read --acids--.

Column 17, line 9 "pod ions" should read --portions--.

Column 18, line 67 "Protoper" should read --Protopet--.

Signed and Sealed this

Eighth Day of December, 1998

Attest:

Attesting Officer

BRUCE LEHMAN

Commissioner of Patents and Trademarks